(12) United States Patent
Grubbs et al.

(10) Patent No.: US 6,610,626 B2
(45) Date of Patent: Aug. 26, 2003

(54) HIGHLY ACTIVE METATHESIS CATALYSTS GENERATED IN SITU FROM INEXPENSIVE AND AIR STABLE PRECURSORS

(75) Inventors: Robert H. Grubbs, South Pasadena, CA (US); Janis Louie, Salt Lake City, UT (US); John P. Morgan, Pasadena, CA (US); Jason L. Moore, Huntsville, TX (US)

(73) Assignees: Cymetech, LLP, Huntsville, TX (US); California Institute of Technology, Pasadena, CA (US)

( * ) Notice: Subject to any disclaimer, the term of this patent is extended or adjusted under 35 U.S.C. 154(b) by 0 days.

(21) Appl. No.: 09/948,115

(22) Filed: Sep. 5, 2001

(65) Prior Publication Data

US 2002/0058812 A1 May 16, 2002

Related U.S. Application Data

(60) Provisional application No. 60/230,547, filed on Sep. 5, 2000, provisional application No. 60/278,311, filed on Mar. 23, 2001, provisional application No. 60/288,680, filed on May 3, 2001, provisional application No. 60/309,806, filed on Aug. 1, 2001, and provisional application No. 60/281,046, filed on Apr. 2, 2001.

(51) Int. Cl.$^7$ .......................... B01J 31/00; C07F 15/00; C07F 17/02
(52) U.S. Cl. .................. 502/155; 502/167; 548/101; 548/103; 556/136
(58) Field of Search ................. 502/155, 167; 556/136; 548/101, 103

(56) References Cited

U.S. PATENT DOCUMENTS

| | | | |
|---|---|---|---|
| 5,342,909 A | 8/1994 | Grubbs et al. | 526/171 |
| 5,710,298 A | 1/1998 | Grubbs et al. | 556/22 |
| 5,728,785 A | 3/1998 | Grubbs et al. | 526/142 |
| 5,728,917 A | 3/1998 | Grubbs et al. | 585/653 |
| 5,750,815 A | 5/1998 | Grubbs et al. | 585/511 |
| 5,831,108 A | 11/1998 | Grubbs et al. | 556/21 |
| 5,917,071 A * | 6/1999 | Grubbs et al. | 502/152 |
| 5,939,504 A * | 8/1999 | Woodson, Jr. et al. | 502/155 |
| 6,107,420 A * | 8/2000 | Grubbs et al. | 502/152 |
| 6,175,047 B1 * | 1/2001 | Hori et al. | 502/152 |
| 6,225,488 B1 * | 5/2001 | Mukerjee et al. | 502/155 |
| 6,271,315 B1 * | 8/2001 | Kiessling et al. | 526/172 |
| 6,291,616 B1 * | 9/2001 | Kiessling et al. | 526/172 |
| 6,313,365 B1 * | 11/2001 | Hori et al. | 502/162 |
| 6,426,419 B1 * | 7/2002 | Grubbs et al. | 502/155 |
| 2001/0006988 A1 * | 7/2001 | Kuhnle et al. | 526/172 |
| 2001/0049398 A1 * | 12/2001 | Olivier-Bourbigou et al. | 502/162 |
| 2002/0022741 A1 * | 2/2002 | Pederson et al. | 502/162 |
| 2002/0107138 A1 * | 8/2002 | Hoveyda et al. | 502/167 |

FOREIGN PATENT DOCUMENTS

| | | | |
|---|---|---|---|
| DE | 44 47 066 A 1 * | 7/1996 | |
| EP | 0 798 041 A1 * | 3/1997 | |
| EP | 0 921 129 * | 6/1999 | |
| JP | 270892 A | 10/2001 | C07F/15/00 |
| WO | WO0015339 | 3/2000 | B01J/31/00 |

OTHER PUBLICATIONS

A. Wolinska et al., J. Organomet. Chem., vol. 420, pp. 217–226 (1991).*

L. Jafarpour et al., Organometallics, vol. 18, No. 18, pp. 3760–3763 (1999).*

H.–J. Schanz et al., Organometallics, vol. 18, No. 24, pp. 5187–5190 (1999).*

(List continued on next page.)

Primary Examiner—Mark L. Bell
Assistant Examiner—J. Pasterczyk
(74) Attorney, Agent, or Firm—David Jaffer; Pillsbury Winthrop LLP

(57) ABSTRACT

The invention provides a process for the in-situ generation of a metathesis active catalyst of the formula:

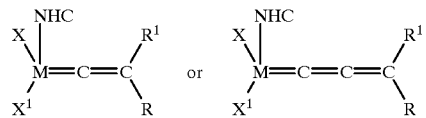

comprising contacting an NHC carbene with a dimer of the formula [(arene)MX$^1$X]$_2$ and an

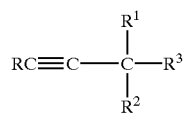

alkyne of the formula RC≡CR$^1$ or wherein M is ruthenium or osmium;

X and X$^1$ are the same or different and are each independently an anionic ligand;

NHC is any N-heterocyclic carbene ligand;

R, R$^1$ and R$^2$ are each independently hydrogen or a substituted or unsubstituted substituent selected from the group consisting of C$_1$–C$_{20}$ alkyl, C$_2$–C$_{20}$ alkenyl, C$_2$–C$_{20}$ alkynyl, aryl, C$_1$–C$_{20}$ carboxylate, C$_1$–C$_{20}$ alkoxy, C$_2$–C$_{20}$ alkenyloxy, C$_2$–C$_{20}$ alkynyloxy, aryloxy, C$_2$–C$_{20}$ alkoxycarbonyl, C$_1$–C$_{20}$ alkylthio, C$_1$–C$_{20}$ alkylsulfonyl and C$_1$–C$_{20}$ alkylsulfinyl; and R$^3$ is OH.

Preferably, the NHC is an s-IMES or IMES carbene ligand; the arene is preferably p-cymene and the alkyne is preferably acetylene. The invention further provides a process for ROMP and RCM reactions using the metathesis active catalysts.

15 Claims, No Drawings

OTHER PUBLICATIONS

T. Westkamp et al., Agnew. Chem. Int. Ed. Engl., vol. 37, No. 18, pp. 2490–2493, 1998.*

M. Buchmeiser, Chem. Rev., vol. 100, pp. 1565–1604, 2000.*

T. Trnka et al., Acc. Chem. Res., vol. 34, pp. 18–29, 2001.*

Grubbs, et al. "Ring–Closing Metathesis and Related Processes in Organic Synthesis" Acc. Chem. Res. 1995, 28, pp 446–452.

Nguyen, et al. "Synthesis and Activities of New Single–Component, Ruthenium–Based Olefin Metathesis Catalysts" Journal of the American Chemical Society, 1993, 115, pp. 9858–9859.

Le Bozec, et al "A New Route To Vinylcarbene Metal Complexes in One Step from 2–Propyn–1–ols and Arene Ruthenium(II) Derivatives" Journal Chemical Society, Chem. Commun. 1989, pp. 219–221.

Dias, et al. "Well–Defined Ruthenium Olefin Metathesis Catalysts: Mechanism and Activity" Journal of the American Chemical Society 1997, 119, pp 3887–3897.

* cited by examiner

HIGHLY ACTIVE METATHESIS CATALYSTS GENERATED IN SITU FROM INEXPENSIVE AND AIR STABLE PRECURSORS

This application claims the benefit of U.S. Provisional Application No. 60/230,547, filed Sep. 5, 2000, entitled HIGHLY ACTIVE METATHESIS CATALYSTS GENERATED IN SITU FROM INEXPENSIVE AND AIR STABLE PRECURSORS; U.S. Provisional Application No. 60/278,311 filed Mar. 23, 2001; U.S. Provisional Application No. 60/288,680 filed May 3, 2001; U.S. Provisional Application No. 60/309,806 filed Aug. 1, 2001 and U.S. Provisional Application No. 60/281,046 filed Apr. 2, 2001, the contents of each of which are incorporated herein by reference.

The U.S. Government has certain rights in this invention pursuant to Grant No. 3 RO1 GM 31332-16 awarded by the National Institute of Health and Grant No. CHE-9809856 awarded by the National Science Foundation.

BACKGROUND

Metathesis catalysts have been previously described by for example, U.S. Pat. Nos. 5,312,940, 5,342,909, 5,728,917, 5,750,815, 5,710,298, and 5,831,108 and PCT Publications WO 97/20865 and WO 97/29135 which are all incorporated herein by reference. These publications describe well-defined single component ruthenium or osmium catalysts that possess several advantageous properties. For example, these catalysts are tolerant to a variety of functional groups and generally are more active than previously known metathesis catalysts. In an unexpected and surprising result, the inclusion of an N-heterocyclic carbene ligand in these metal-carbene complexes had been found to dramatically improve the already advantageous properties of these catalysts. The preparation of well-defined ruthenium alkylidene complexes bearing N-heterocyclic carbene ligands such as 1,3-dimesitylimidazol-2-ylidene and 4,5-dihydroimidazol-2-ylidene, have led to other catalysts which are highly active in metathesis reactions, including ring-closing metathesis (RCM), acyclic diene metathesis (ADMET), cross metathesis (CM), and ring-opening metathesis polymerization (ROMP). These catalysts show increased thermal stability and similar tolerance to oxygen and moisture when compared to their parent bisphosphine complexes, $Cl_2(PCy_3)_2Ru=CHR$. However, since all synthetic routes to the N-heterocyclic carbene complexes proceed through transformation of a ruthenium bisphosphine carbene, a direct route through readily available starting materials is still needed.

SUMMARY

The invention relates to preparing and measuring the metathesis activity of ruthenium vinylidene and cumulene complexes bearing an N-heterocyclic ligand. The catalysts used in the present invention are of the general formula:

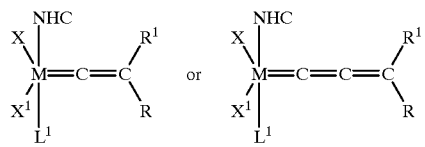

wherein
M is ruthenium or osmium;
X and $X^1$ are the same of different and are each independently an anionic ligand;
NHC is any N-heterocyclic carbene ligand;
$L^1$ is any neutral electron donor ligand; and,
R, $R^1$ and $R^2$ are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Optionally, each of the R, $R^1$, or $R^2$ substituent group may be substituted with one or more moieties selected from the group consisting of $C_1$–$C_{10}$ alkyl, $C_1$–$C_{10}$ alkoxy, and aryl which in turn may each be further substituted with one or more groups selected from a halogen, a $C_1$–$C_5$ alkyl, $C_1$–$C_5$ alkoxy, and phenyl. Moreover, any of the catalyst ligands may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen. Examples of N-heterocyclic carbene ligands include:

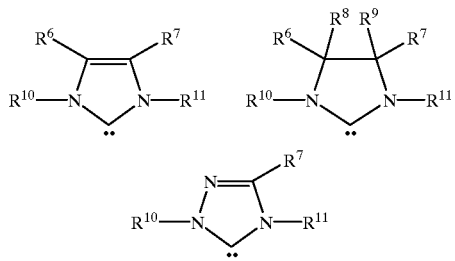

wherein $R^6$, $R^7$, $R^8$, $R^9$, $R^{10}$ and $R^{11}$ are each independently hydrogen or a substituent selected from the group consisting of $C_1$–$C_{20}$ alkyl, $C_2$–$C_{20}$ alkenyl, $C_2$—$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Optionally, each of the R, $R^1$, $R^2$, $R^6$, $R^7$, $R^8$, $R^9$, $R^{10}$ and $R^{11}$ substituent group may be substituted with one or more moieties selected from the group consisting of $C_1$–$C_{10}$ alkyl, $C_1$–$C_{10}$ alkoxy, and aryl which in turn may each be further substituted with one or more groups selected from a halogen, a $C_1$–$C_5$ alkyl, $C_1$–$C_5$ alkoxy, and phenyl. Moreover, any of the catalyst ligands may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

DETAILED DESCRIPTION OF THE PREFERRED EMBODIMENTS

The invention relates to preparing and measuring the metathesis activity of various ruthenium vinylidene and cumulene complexes bearing N-heterocyclic carbene ligands. In particular, the invention provides for the preparation of novel ruthenium and osmium vinylidene and cumulene complexes bearing at least one N-heterocyclic carbene ligand and measures their activity in ring-opening metathesis polymerization reactions, acyclic diene metathesis reactions, ring-closing metathesis reactions, and cross-metathesis reactions. The invention further relates to the generation of these catalysts in situ with air-stable components. The terms "catalyst" and "complex" herein are used interchangeably.

Unmodified ruthenium and osmium carbene complexes have been described in U.S. Pat. Nos. 5,312,940, 5,342,909, 5,728,917, 5,750,815, and 5,710,298, all of which are incorporated herein by reference. The ruthenium and osmium carbene complexes disclosed in these patents all possess metal centers that are formally in the +2 oxidation state, have an electron count of 16, and are penta-coordinated. These catalysts are of the general formula

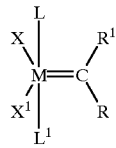

wherein:

M is ruthenium or osmium;

X and $X^1$ are each independently any anionic ligand;

L and $L^1$ are each independently any neutral electron donor ligand;

R and $R^1$ are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Optionally, each of the R or $R^1$ substituent group may be substituted with one or more moieties selected from the group consisting of $C_1$–$C_{10}$ alkyl, $C_1$–$C_{10}$ alkoxy, and aryl which in turn may each be further substituted with one or more groups selected from a halogen, a $C_1$–$C_5$ alkyl, $C_1$–$C_5$ alkoxy, and phenyl. Moreover, any of the catalyst ligands may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

More recently, and as described in PCT Publication Nos. WO 99/51344, WO 00/58322, and WO 00/71554, the contents of each of which are incorporated herein by reference, catalysts bearing an N-heterocyclic ligand have shown increased thermal stability. These catalysts are as described above except that L is an unsubstituted or substituted n-heterocyclic carbene ligand of the general formula:

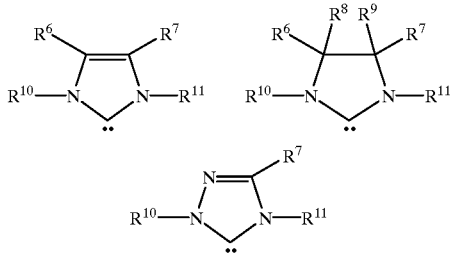

wherein:

$R^6$, $R^7$, $R^8$, $R^9$, $R^{10}$ and $R^{11}$ are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Optionally, each of the R, $R^1R^6$, $R^7$, $R^8$, $R^9$, $R^{10}$ and $R^{11}$ substituent group may be substituted with one or more moieties selected from the group consisting of $C_1$–$C_{10}$ alkyl, $C_1$–$C_{10}$ alkoxy, and aryl which in turn may each be further substituted with one or more groups selected from a halogen, a $C_1$–$C_5$ alkyl, $C_1$–$C_5$ alkoxy, and phenyl. Moreover, any of the catalyst ligands may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen. The inclusion of an NHC ligand to the ruthenium or osmium catalysts has been found to dramatically improve the properties of these complexes.

In preferred embodiments of the inventive catalysts, the R substituent is hydrogen and the $R^1$ substituent is selected from the group consisting of $C_1$–$C_{20}$ alkyl, $C_2$–$C_{20}$ alkenyl, and aryl. In even more preferred embodiments, the $R^1$ substituent is phenyl or vinyl, optionally substituted with one or more moieties selected from the group consisting of $C_1$–$C_5$ alkyl, $C_1$–$C_5$ alkoxy, phenyl, and a functional group. In especially preferred embodiments, $R^1$ is phenyl or vinyl substituted with one or more moieties selected from the group consisting of chloride, bromide, iodide, fluoride, —$NO_2$, —$NMe_2$, methyl, methoxy and phenyl. In the most preferred embodiments, the $R^1$ substituent is phenyl or —C=C(CH_3)_2.

In preferred embodiments of the inventive catalysts, $L^1$ is selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether. In more preferred embodiments, $L^1$ is a phosphine of the formula $PR^3R^4R^5$, where $R^3$, $R^4$, and $R^5$ are each independently aryl or $C_1$–$C_{10}$ alkyl, particularly primary alkyl, secondary alkyl or cycloalkyl. In the most preferred embodiments, $L^1$ is each selected from the group consisting of —P(cyclohexyl)$_3$, —P(cyclopentyl)$_3$, —P(isopropyl)$_3$, and —P(phenyl)$_3$.

In preferred embodiments of the inventive catalysts, X and $X^1$ are each independently hydrogen, halide, or one of the following groups: $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, $C_1$–$C_{20}$ alkylsulfonyl, or $C_1$–$C_{20}$ alkylsulfinyl. Optionally, X and $X^1$ may be substituted with one or more moieties selected from the group consisting of $C_1$–$C_{10}$ alkyl, $C_1$–$C_{10}$ alkoxy, and aryl which in turn may each be further substituted with one or more groups selected from halogen, $C_1$–$C_5$ alkyl, $C_1$–$C_5$ alkoxy, and phenyl. In more preferred embodiments, X and $X^1$ are halide, benzoate, $C_1$–$C_5$ carboxylate, $C_1$–$C_5$ alkyl, phenoxy, $C_1$–$C_5$ alkoxy, $C_1$–$C_5$ alkylthio, aryl, and $C_1$–$C_5$ alkyl sulfonate. In even more preferred embodiments, X and $X^1$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate. In the most preferred embodiments, X and $X^1$ are each chloride.

In preferred embodiments of the inventive catalysts, $R^6$ and $R^7$ are each independently hydrogen, phenyl, or together form a cycloalkyl or an aryl optionally substituted with one or more moieties selected from the group consisting of $C_1$–$C_{10}$ alkyl, $C_1$–$C_{10}$ alkoxy, aryl, and a functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen; and $R^8$ and $R^9$ are each is independently $C_1$–$C_{10}$ alkyl or aryl optionally substituted with $C_1$–$C_5$ alkyl, $C_1$–$C_5$ alkoxy, aryl, and a functional group selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

In more preferred embodiments, $R^6$ and $R^7$ are both hydrogen or phenyl, or $R^6$ and $R^7$ together form a cycloalkyl group; and $R^8$ and $R^9$ are each either substituted or unsubstituted aryl. Without being bound by theory, it is believed that bulkier $R^8$ and $R^9$ groups result in catalysts with improved characteristics such as thermal stability. In especially preferred embodiments, $R^8$ and $R^9$ are the same and each is independently of the formula

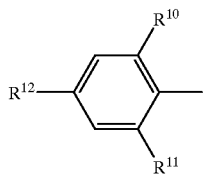

wherein:

$R^{10}$, $R^{11}$, and $R^{12}$ are each independently hydrogen, $C_1$–$C_{10}$ alkyl, $C_1$–$C_{10}$ alkoxy, aryl, or a functional group selected from hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen. In especially preferred embodiments, $R^{10}$, $R^{11}$, and $R^{12}$ are each independently selected from the group consisting of hydrogen, methyl, ethyl, propyl, isopropyl, hydroxyl, and halogen. In the most preferred embodiments, $R^{10}$, $R^{11}$, and $R^{12}$ are the same and are each methyl.

Examples of the most preferred embodiments of the complexes include:

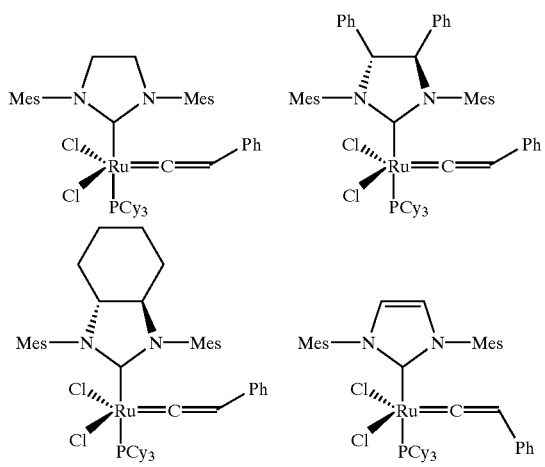

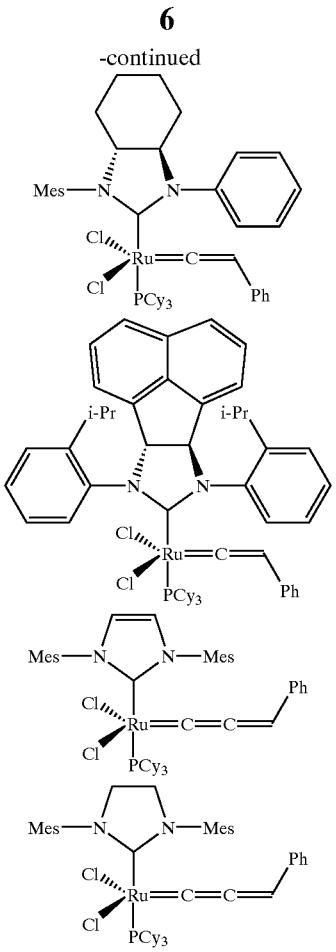

wherein Mes is

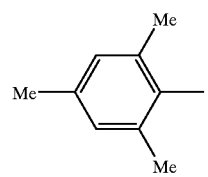

(also known as "mesity"); i—Pr is isopropyl; and $PCy_3$ is —P(cyclohexyl)$_3$.

In all of the above carbene complexes, at least one of $L^1$, X, $X^1$, R and $R^1$, may be linked to at least one other of $L^1$, X, $X^1$, R and $R^1$ to form a bidentate or multidentate ligand array.

In Situ Generation of Catalysts

Ruthenium or osmium vinylidenes can be easily prepared from commercially available terminal alkynes and ruthenium sources. Unfortunately, such complexes have only been active in the ROMP of highly strained norbomenes. Without being bound by theory, it is believed that the mechanism of olefin metathesis is dissociative in ligand, i.e., phosphine or imidazolylidene, and it is well known that the latter ligands have relatively higher binding energies. The invention shows that carbenes bearing a mixed ligand set, i.e., one imidazolylidene and one phosphine, have pronounced activities.

The invention provides a process for the ring-closing metathesis of acyclic olefins using a ruthenium or osmium vinylidene or cumulene complex. Scheme 1 provides a general reaction scheme for this process:

SCHEME 1

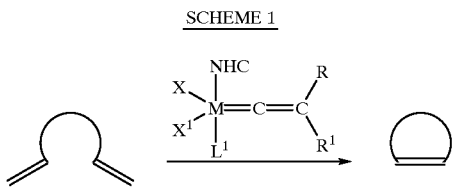

wherein M, X, $X^1$, $L^1$, NHC, R and $R^1$ are as defined above. Again, a cumulene complex in accordance with the principles of the invention may also be used in the ring-closing metathesis reaction.

The vinylidenes and cumulenes may be prepared by simple ligand exchange as shown in Scheme 2:

SCHEME 2

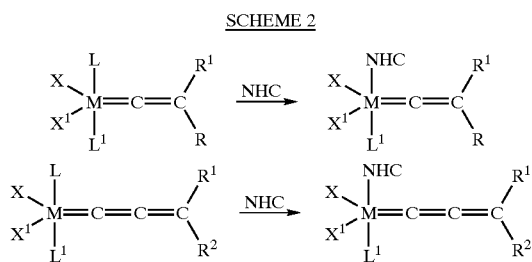

wherein M, X, $X^1$, $L^1$, R, $R^1$ and $R^2$ are as defined above.

For example, a ruthenium vinylidene possessing a mixed ligand system was prepared and investigated for RCM. Simple phosphine displacement of the known $Cl_2(PCy_3)_2Ru=C=CH^tBu$ with bulky 1,3-dimesitylimidazol-2-ylidene (1) afforded $Cl_2(PCy_3)(Imes)Ru=C=CH^tBu$ 8 in 85% yield as a brown solid. Complex 8 catalyzed the RCM of diethyl diallylmalonate in 86% yield (Table 1, entry 1a). Although the reaction rate was much slower than ruthenium alkylidenes, this was the first example of RCM catalyzed by a ruthenium vinylidene complex. By metathesis active catalyst, it is meant that the catalyst is in a low-coordination state, for example a tetracoordinated complex. Without being bound by theory, it is believed that the slow rate of reaction may result from slow initiation since the propagating species (methylidene) is identical to one produced by carbene complex $Cl_2(PCy_3)(Imes)Ru=CHPh$ 3.

Further, and without being bound by theory, it is believed that these results show ligand dissociation (i.e., phosphine) was necessary to increase catalytic activity. Previously, addition of phosphine sponges, such as copper salts or acid, has been used to facilitate RCM catalyzed by ruthenium carbenes. An alternative approach would involve the direct generation of the phosphine-free active species in situ, thus circumventing the need for adding additional reagents to remove phosphine. The general reaction scheme for generating the metathesis active species in situ begins with the generation of an NHC carbene from the NHC carbene salt as shown in Scheme 3:

SCHEME 3

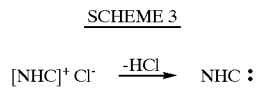

The NHC carbene may also be generated using a "protected" NHC, for example, an s-IMES $HCCl_3$ ligand. A discussion of protected NHC carbenes can be seen, for example, in U.S. application Nos. 60/288,680 filed May 3, 2001, and U.S. Provisional Application No. 60/309,806, the contents of each of which are incorporated herein by reference. The NHC carbene is then contacted with a ruthenium or osmium source, for example, a ruthenium chloride monomer or dimer, as shown in Scheme 4:

SCHEME 4

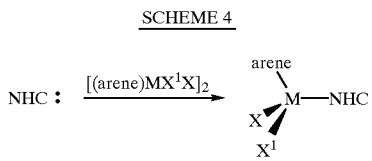

Monomers that provide a ruthenium or osmium source include $((C_6H_{11})_2HPRu(p\text{-cymene})Cl_2$, $(C_6H_{11})_3PRu(p\text{-cymene})Cl_2$, $(C_6H_{11})_3PRu(p\text{-cymene})(tos)_2$, $(C_6H_{11})_3PRu(p\text{-cymene})BR_2$, $(C_6H_{11})_3PRu(p\text{-cymene})ClF$, $(C_6H_{11})_3PRu(C_6H_6)(tos)_2$, $(C_6H_{11})_3PRu(CH_3-C_6H_5)(tos)_2$, $(C_6H_{11})_3PRu(C_{10}H_8)(tos)_2$, $(I-C_3H_7)_3PRup\text{-cymene})Cl_2$, $(CH_3)_3PRu(p\text{-cymene})Cl_2$, $(C_6H_{11})_3PRu(CH_3-CN(C_2H_5-OH))(tos)_2$, $(C_6H_{11})_3PRu(p\text{-cymene})CH_3-CN)_2$, $(PF_6)_2(C_6H_{11})_3PRu(p\text{-cymene})(CH_3-CN)_2(tos)_2$, $(n-C_4H_9)_3PRu(p\text{-cymene})CH_3-CN)_2(tos)_2$, $(C_6H_{11})_3PRu(CH_3CN)Cl_2$, $(C_6H_{11})_3PRu(CH_3-CN)_2Cl_2$, $(n-C_4C_4H_9)_3PRu(p\text{-cymene})Cl_2$, $(C_6H_{11})_3PRu(p\text{-cymene})C_2H_5OH)_2(BF_4)_2$, $(C_6H_{11})_3PRu(p\text{-cymene})(C_2H_5OH)_2(PF_6)_2$, $(i-C_3H_7)_3POs(p\text{-cymene})Cl_2$, $(CH_3)_3POs(p\text{-cymene})Cl_2$, $(C_6H_5)_3POs(p\text{-cymene})Cl_2$, $[(C_8H_{11})_3P]_3Ru(CH_3-CN)$, $(C_5H_9)_3PRu(p\text{-cymene})Cl_2$, $(C_6H_{11})_3PRu(p\text{-cymene})HCl$, $(C_6H_{11})_3PRu[1,2,4,5-(CH_3)_4(C_6H_2]Cl_2$, $(C_6H_{11})_3PRu[1,3,5-(i-C_3H_7)_3C_6H_3]Cl_2$, $(C_6H_{11})_3PRu[(C_6H_9)-C_6H_5]Cl_2$, $(C_6H_{11})_3POs(p\text{-cymene})Cl_2$, $(C_6H_5)_3PRu(p\text{-cymene})HCl$, $[(C_6H_{11})_3P]_2Ru(CH_3-CN)(tos)_2$, $RuCl_2(p\text{-cymene})[(C_6H_{11})_2PCH_2CH_2P(C_6H_{11})_2]$, $(C_6H_{11})_3PRu(p\text{-cymene})(C_2H_5OH)BF_4)_2$, $(C_6H_{11})_3PRu(C_6H_6)(C_2H_5OH)_2(tos)_2$, $(C_6H_{11})_3PRu(i-C_3H_7-C_6H_5)(tos)_2$, $(C_6H_{11})_3PRu(C_6H_6)(p\text{-cymene})Br_2$, $(C_6H_{11})_3PRu(biphenyl)(tos)_2$, $(C_6H_{11})_3PRu(anthracene)(tos)_2$, $(2-CH_3C_6H_4)_3POs(p\text{-cymene})Cl_2$, and $(C_6H_{11})_3PRu(chrysene)(tos)_2$.

Any substituted or unsubstituted arene may be used, for example p-cymene or tolyls. Preferably, the arene is p-cymene.

Preferably, the NHC product from Scheme 4 is then contacted with an alkyne, preferably acetylene, to form the tetracoordinated metathesis active compound as shown in Scheme 5:

SCHEME 5

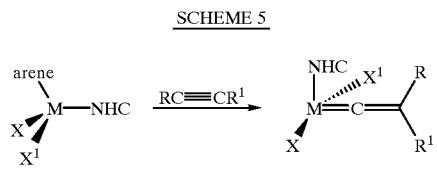

Other alkynes that may be used include ethyne, phenylethyne, 4-tert-butylphenylethyne, trimethylsilylethyne, and triethylsilylethyne. A more descriptive list of alkynes that may be used in accordance with the principles of the invention can be seen in U.S. Pat. No. 6,171,995, the contents of which are incorporated herein by reference.

Metathesis active cumulene complexes can be formed in situ in a similar manner as shown in Scheme 6:

SCHEME 6

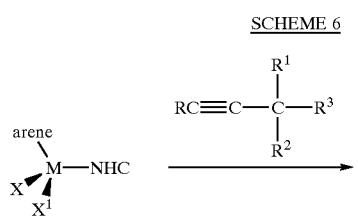

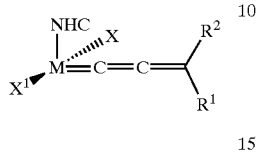

In all of the above schemes, NHC, M, X, X$^1$, R, R$^1$ and R$^2$ are as defined above, and R$^3$ is OH.

Preferred embodiments of the metathesis active catalysts are

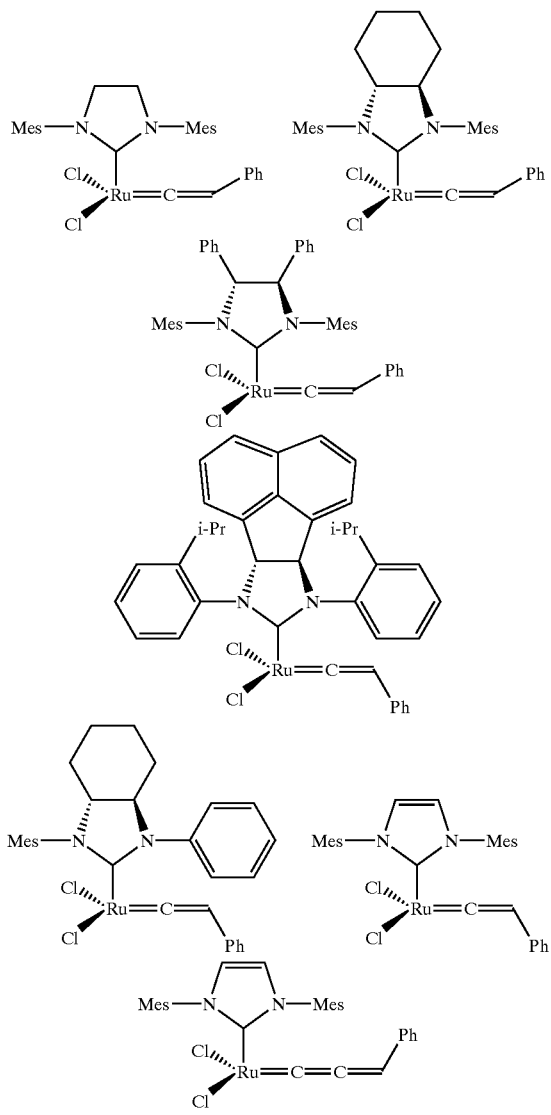

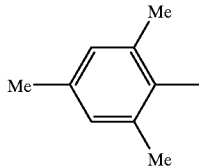

wherein Mes is (also known as "mesityl"); i—Pr is isopropyl; and PCy$_3$ is —P(cyclohexyl)$_3$.

Schemes 7–8 illustrate the generation of the preferred metathesis active vinylidene compound:

SCHEME 7

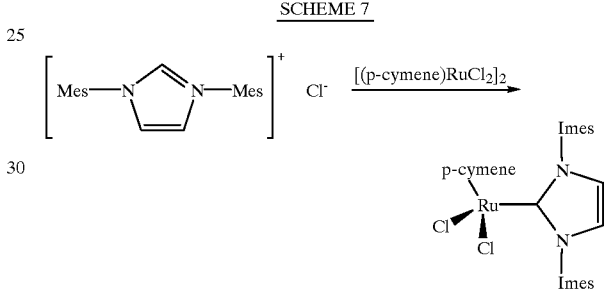

SCHEME 8

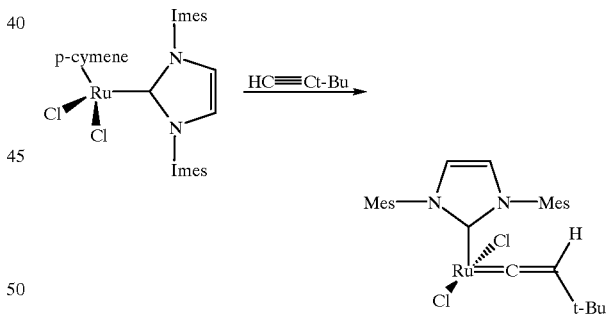

For example, ruthenium vinylidenes can be conveniently prepared by adding 2 equivalents of phosphine and a terminal alkyne to [(p-cymene)RuCl$_2$]$_2$ (9). Table 1 shows the results of metathesis reactions using [(p-cymene)RuCl$_2$]$_2$/ 1Cl/tert-butyl acetylene where E=CO$_2$Et unless otherwise indicated. The percent yield are the isolated yields and for entries 1a–f, the percent yield was determined using $^1$H NMR. In addition, for entries 1c–d, the percent yield represents the percent conversion. As shown in Table 1 (entry 1b), the combination of 2.5 mol % dimer 9, 5 mol % 1,3-dimesitylimidazol-2-ylidene (1), and 5 mol % of tert-butyl acetylene generated phosphine-free Cl$_2$(Imes)Ru=C=CH$^t$Bu in situ, which subsequently catalyzed the RCM of diethyl diallylmalonate affording the ring-closed product in 95% yield (80° C., 12h, entry 1b). The reaction shown in entry 1b was performed with ligand 1 using toluene as a solvent.

TABLE 1

| | Substrate | Product | Time | Yield |
|---|---|---|---|---|
| 1a | (diallyl with E,E quaternary C) | (cyclopentene with E,E) | 24 h[a] | 86[c] |
| b | | | 12 h[e,f] | 95[c] |
| c | | | 2 h[e,f,h] | 51[c,i] |
| d | | | 2 h[e,f] | 86[c,i] |
| e | | | 2 h[e,g,h] | 44[c] |
| f | | | 2 h[e,g] | 73[c] |
| g | | | 10 h | 96 |
| h | | | 10 h[h] | 0 |
| 2 | (allyl/methallyl with E,E) | (methylcyclopentene with E,E) | 10 h | 98 |
| 3 | (allyl/isopropylidene with E,E) | (isopropylcyclopentene with E,E) | 24 h | 96 |
| 4 | (bis-methallyl with E,E) | (dimethylcyclohexene with E,E) | 24 h | 79 |
| 5 | (homoallyl/methallyl with E,E) | (methylcycloheptene with E,E) | 10 h | 76 |
| 6 | (allyl/propynyl with E,E) | (isopropenylcyclopentene with E,E) | 10 h | 80 |
| 7 | (allylbenzene) | (1,3-diphenylpropene) | 8 h | 93 |
| 8 | (cyclooctadiene)n | (polymer, 2n) | 1 h[j] | 95 |

The complex formed in situ displayed higher catalytic activity than Cl$_2$(Imes)(PCy$_3$)Ru=C=CH$^t$Bu vinylidene (8) (86%, 65° C., 24 h) which further suggests that a vinylidene possessing a low coordination number may be necessary for initiation.

The scope of the reagents needed to generate vinylidene catalysts in situ was investigated further. As expected, the absence of a ruthenium source or NHC ligand failed to provide any ring-closed product. While the absence of alkyne did provide ring-closed product, the reaction rates were slower (Table 1, entries 1c–d). The reactions shown in entries 1c and 1d also were performed with ligand 1 using toluene as a solvent; however, no tert-butyl acetylene was added in the reaction shown in entry 1d. Presumably, (P-cymene) (IMes)RuCl$_2$, a known RCM catalyst precursor, is being generated in situ. However, the inclusion of alkyne resulted in substantially higher yields when the RCM reaction was performed in THF (entries 1e–f). The reactions shown in both entries 1e and 1f were performed with ligand 1 using THF as a solvent; however, no tert-butyl acetylene was added in the reaction shown in entry 1e. Thus, while the inventive process may be performed in the absence of a solvent, it is apparent from these control reactions that solvent plays an important role in the generation of a metathesis catalyst in situ.

Various solvents may be used with the inventive method. Examples of solvents that can be used in the polymerization reaction include organic, protic, or aqueous solvents, which are preferably inert under the polymerization conditions. Examples of such solvents include aromatic hydrocarbons, chlorinated hydrocarbons, ethers, aliphatic hydrocarbons, alcohols, water, or mixtures thereof. Preferred solvents include benzene, toluene, p-xylene, methylene chloride, dichloroethane, dichlorobenzene, chlorobenzene, tetrahydrofuran, diethylether, pentane, methanol, ethanol, water or mixtures thereof. More preferably, the solvent is hexane, benzene, toluene, p-xylene, methylene chloride, dichloroethane, dichlorobenzene, chlorobenzene, tetrahydrofuran, diethylether, pentane, methanol, ethanol, or mixtures thereof. Most preferably, the solvent is hexane. The solubility of the polymer formed in the polymerization reaction will depend on the choice of solvent and the molecular weight of the polymer obtained.

Although a number of imidazolylidenes are stable as their free carbene, an easier method would involve the generation of the free imidazolylidene carbene in situ from the appropriate salt and base. Such a method has been used to generate NHC ligand based vinyl alkylidene complexes, such as Cl$_2$(PCy3)(s-IMES)Ru=CH—CH=C(CH$_3$)$_2$ (3) and Cl(PCy$_3$)$_2$RuH(H$_2$) (4) as well as a palladium aryl amination catalyst. In hopes of extending this methodology to include metathesis reactions, the RCM of diethyl diallylmalonate using [(p-cymene)RuCl$_2$]$_2$, NaO$^t$Bu, and each of the NHC salts shown below:

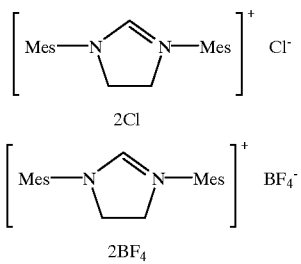

2Cl

2BF$_4$

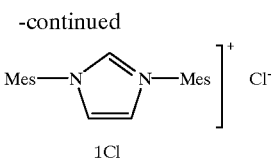

1Cl under various conditions. Unfortunately, all RCM reactions with ligand 2X (X=BF$_4$, Cl) failed to give cyclized product and may be related to the instability of the saturated imidazolylidene free carbene. Alternatively, the formation of the vinylidene precursor may be blocked due to deprotonation of the alkyne by base, although addition of alkyne as the final reagent still afforded only starting material. Similar results were obtained with 1Cl when the reactions were performed in either toluene or TEF. However, dramatically different results were obtained in hexanes. As shown in entry 1 g (Table 1), diethyl diallylmalonate was converted to the corresponding ring-closed product in 96% yield. The addition of alkyne was imperative as no product was observed in its absence (entry 1 h). Without being bound by theory, it is possible that a highly unstable and unsaturated alkoxide ruthenium complex is generated from the presence of NaOtBu. The combination of a low concentration of metal complex soluble in hexanes as well as the generation of a vinylidene complex from the addition of alkyne may produce a stable ruthenium vinylidene species resistant to decomposition (Scheme 10).

SCHEME 10

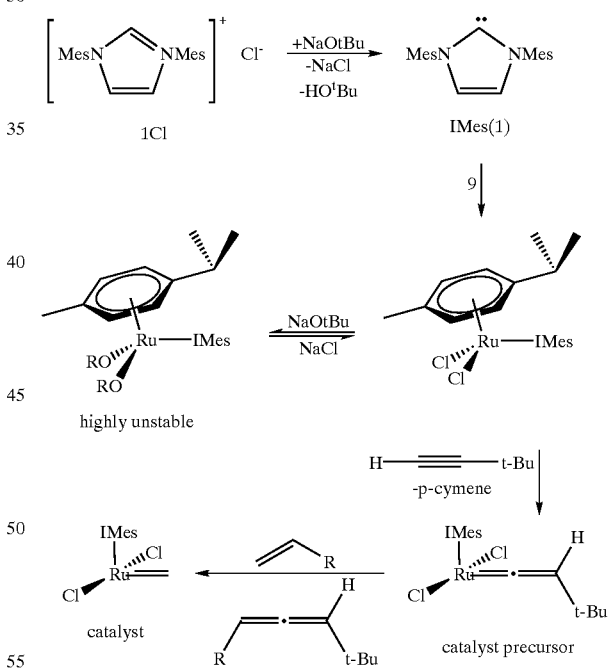

As stated above, a variety of metathesis reactions were performed using this system (Table 1). Interestingly, in addition to RCM, the catalyst generated in situ was also effective in CM, ene-yne metathesis, ROMP, and ADMET. While reaction times were longer, sterically hindered olefins were cyclized in high in comparable yields to those obtained using complexes 3 and 4. As demonstrated in Table 1, the invention provides a process to generate a highly active metathesis catalyst, capable of ring-closing both trisubstituted and tetrasubstituted olefins, from inexpensive materials.

The metathesis active catalysts generated in situ are also useful in ring-opening metathesis polymerization (ROMP) reactions of strained or unstrained cyclic olefins. ROMP reactions follow the general scheme:

SCHEME 11

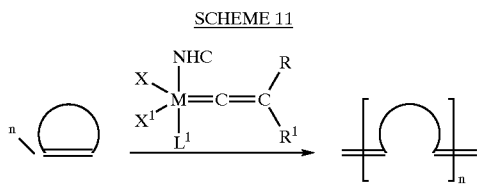

wherein M, X, X$^1$, L$^1$, NHC, R and R$^1$ are as defined above. Again, cumulene complexes in accordance with the principles of the invention may also be used.

The most preferred cyclic olefin monomer for use in ROMP reactions in accordance with the principles of the invention is substituted or unsubstituted dicyclopentadiene (DCPD). Various DCPD suppliers and purities may be used such as Lyondell 108 (94.6% purity), Veliscol UHP (99+% purity), B. F. Goodrich Ultrene® (97% and 99% purities), and Hitachi (99+% purity). Other preferred olefin monomers include other cyclopentadiene oligomers including trimers, tetramers, pentamers, and the like; cyclooctadiene (COD; DuPont); cyclooctene (COE, Alfa Aesar); cyclohexenylnorbornene (Shell); norbornene (Aldrich); norbornene dicarboxylic anhydride (nadic anhydride); norbornadiene (Elf Atochem); and substituted norbornenes including butyl norbornene, hexyl norbornene, octyl norbornene, decyl norbornene, and the like. Preferably, the olefinic moieties include mono-or disubstituted olefins and cycloolefins containing between 3 and 200 carbons. Most preferably, metathesis-active olefinic moieties include cyclic or multicyclic olefins, for example, cyclopropenes, cyclobutenes, cycloheptenes, cyclooctenes, [2.2.1]bicycloheptenes, [2.2.2] bicyclooctenes, benzocyclobutenes, cyclopentenes, cyclopentadiene oligomers including trimers, tetramers, pentamers, and the like; cyclohexenes. It is also understood that such compositions include frameworks in which one or more of the carbon atoms carry substituents derived from radical fragments including halogens, pseudohalogens, alkyl, aryl, acyl, carboxyl, alkoxy, alkyl- and arylthiolate, amino, amninoalkyl, and the like, or in which one or more carbon atoms have been replaced by, for example, silicon, oxygen, sulfur, nitrogen, phosphorus, antimony, or boron. For example, the olefin may be substituted with one or more groups such as thiol, thioether, ketone, aldehyde, ester, ether, amine, amide, nitro, carboxylic acid, disulfide, carbonate, isocyanate, phosphate, phosphite, sulfate, sulfite, sulfonyl, carbodiimide, carboalkoxy, carbamate, halogen, or pseudohalogen. Similarly, the olefin may be substituted with one or more groups such as $C_1$–$C_{20}$ alkyl, aryl, acyl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, arylthio, $C_1$–$C_{20}$ alkylsulfonyl, and $C_1$–$C_{20}$ alkylsulfinyl, $C_1$–$C_{20}$ alkylphosphate, arylphosphate, wherein the moiety may be substituted or unsubstituted. Preferably, the olefin monomer is substituted or unsubstituted DCPD. In accordance with the principles of the invention, in a ROMP reaction, the polymer may be formed by a process comprising contacting the olefin monomer, preferably substituted or unsubstituted DCPD, with a ruthenium source such as dimer 9, and a source for the NHC carbene, such as a protected NHC or the NHC salt, preferably the s-IES salt.

These cyclic and acyclic olefin monomers may be used alone or mixed with each other in various combinations to adjust the properties of the olefin monomer composition. For example, mixtures of cyclopentadiene dimer and trimers offer a reduced melting point and yield cured olefin copolymers with increased mechanical strength and stiffness relative to pure poly-DCPD. As another example, incorporation of COD, norbornene, or alkyl norbornene co-monomers tend to yield cured olefin copolymers that are relatively soft and rubbery. The resulting polyolefin compositions formed from the metathesis reactions are amenable to thermosetting and are tolerant of additives, stabilizers, rate modifiers, hardness and/or toughness modifiers, fillers and fibers including, but not limited to, carbon, glass, aramid (e.g., Kevlar® and Twaron®), polyethylene (e.g., Spectra® and Dyneema®), polyparaphenylene benzobisoxazole (e.g., Zylon®), polybenzamidazole (PBI), and hybrids thereof as well as other polymer fibers.

The metathesis reactions may optionally include formulation auxiliaries. Known auxiliaries include antistatics, antioxidants (primary antioxidants, secondary antioxidants, or mixtures thereof), ceramics, light stabilizers, plasticizers, dyes, pigments, fillers, reinforcing fibers, lubricants, adhesion promoters, viscosity-increasing agents, and demolding enhancers. Illustrative examples of fillers for improving the optical physical, mechanical, and electrical properties include glass and quartz in the form of powders, beads, and fibers, metal and semi-metal oxides, carbonates (e.g. $MgCO_3$, $CaCO_3$), dolomite, metal sulfates (e.g. gypsum and barite), natural and synthetic silicates (e.g. zeolites, wollastonite, and feldspars), carbon fibers, and plastics fibers or powders.

The UV and oxidative resistance of the polyolefin compositions resulting from the metathesis reactions using the inventive carbene complex may be enhanced by the addition of various stabilizing additives such as primary antioxidants (e.g., sterically hindered phenols and the like), secondary antioxidants (e.g., organophosphites, thioesters, and the like), light stabilizers (e.g., hindered amine light stabilizers or HALS), and UV light absorbers (e.g., hydroxy benzophenone absorbers, hydroxyphenylbenzotriazole absorbers, and the like), as described in PCT Publication No. WO 00/46256, the contents of which are incorporated herein by reference.

Exemplary primary antioxidants include, for example, 4,4'-methylenebis (2,6-di-tertiary-butylphenol) (Ethanox 702®; Albemarle Corporation), 1, 3, 5-trimethyl-2, 4, 6-tris (3,5-di-tert-butyl-4-hydroxybenzyl) benzene (Ethanox 330®; Albermarle Corporation), octadecyl-3-(3',5'-di-tert-butyl-4'-hydroxyphenyl) propionate (Irganox 1076®; Ciba-Geigy), and pentaerythritol tetrakis(3-(3,5-di-tert-butyl-4-hydroxyphenyl)propionate)(Irganox® 1010; Ciba-Geigy). Exemplary secondary antioxidants include tris(2,4-ditert-butylphenyl)phosphite (Irgafos® 168; Ciba-Geigy), 1:11 (3, 6, 9-trioxaudecyl)bis(dodecylthio)propionate (Wingstay® SN-1; Goodyear), and the like. Exemplary light stabilizers and absorbers include bis(1, 2, 2, 6, 6-pentamethyl-4-piperidinyl)-[[3,5-bis(1,1-dimethylethyl)-4-hydroxyphenyl] methyl]butylmalonate (Tinuvin® 144 HALS; Ciba-Geigy), 2-(2H-benzotriazol-2-yl)-4,6-ditertpentylphenol (Tinuvin® 328 absorber; Ciba-Geigy), 2,4-di-tert-butyl-6-(5-chlorobenzotriazol-2-yl)phenyl (Tinuvin® 327 absorber; Ciba-Geigy), 2-hydroxy-4-(octyloxy)benzophenone (Chimassorb® 81 absorber; Ciba-Geigy), and the like.

In addition, a suitable rate modifier such as, for example, triphenylphosphine (TPP), tricyclopentylphosphine, tricyclohexylphosphine, triisopropylphosphine, trialkylphosphites, triarylphosphites, mixed phosphites, pyridine, or other Lewis base, as described in U.S. Pat. No.

5,939,504 and U.S. application No. 09/130,586, the contents of each of which are herein incorporated by reference, may be added to the olefin monomer to retard or accelerate the rate of polymerization as required.

The resulting polyolefin compositions, and parts or articles of manufacture prepared therefrom, may be processed in a variety of ways including, for example, Reaction Injection Molding (RIM), Resin Transfer Molding (RTM) and vacuum-assisted variants such as VARTM (Vacuum-Assisted RMT) and SCRIMP (Seemann Composite Resin Infusion Molding Process), open casting, rotational molding, centrifugal casting, filament winding, and mechanical machining. These processing compositions are well known in the art. For example, when using a two-component system, the olefin monomer is contacted with the ruthenium source, such as dimer 9, and set aside as the first component. The second component comprises an olefin monomer and a source for the NHC carbene, such as the NHC salt or a protected NHC, such as a s-IMES-HCCl$_3$. The reaction is initiated when the first component is contacted with the second component. Various molding and processing techniques are described, for example, in PCT Publication WO 97/20865, the disclosure of which is incorporated herein by reference.

Another aspect of the inventive process is conducting a ring-closing metathesis reaction or a ring-opening metathesis polymerization reaction in accordance with the principles of the invention without the use of a drybox or vacuum line or special Schlenk equipment using all air-stable starting materials. The solid components (commercially available) were weighed in air into a reaction flask. The atmosphere was purged with argon followed by the addition of reagent grade hexanes, tert-butyl acetylene and diethyl diallylmalonate. After 10 h at 80° C., ring-closed product was obtained in 88% yield. The reaction rate and yield were comparable to when degassed solvents and drybox procedures were employed (96%, Table 1, entry 1 g).

The following examples are illustrative of the invention and it is understood that the invention is not limited to the disclosed embodiments but that various modifications and substitutions can be made thereto as would be apparent to those skilled in the art.

EXAMPLE 1

A synthetic protocol for a representative example of an imidazolidine ligand is as follows. Other N-heterocyclic carbene ligands are made analogously.

Preparation of 1,2-dimesityl ethylenediamine dihydrochloride:

To a solution of diimine (8.0 g, 27.3 mmol) in THF (100 mL) was added NaBH$_4$ (4.24 g, 112.1 mmol) at 0° C. Concentrated HCl (4.5 mL, 2 eq.) was added dropwise over 30 minutes. After the HCl addition, the reaction mixture was stirred at 0° C. for 20 minutes. Then, 3 M HCl (250 mL) was added carefully to the flask at 0° C. and the mixture was stirred for an additional 1 hr., allowing the temperature to rise to ambient temperature. The resulting white precipitates were filtered and washed with water (200 mL) and 5% acetone-ether (150 mL). The product (9.4 g, 93%) was obtained as a white solid and dried in vacuo.

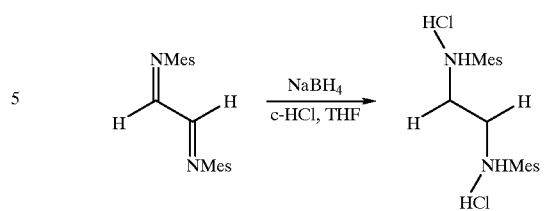

Preparation of 1,3-dimesityl-4,5-dihydro-imidazolium chloride:

To a suspension of the HCl salt (8.5 g, 23 mmol) in HC(OEt)$_3$ (35 mL, 162 mmol) was added 2 drops of HCO$_2$H (adding at 1 mol %). The reaction mixture was then heated at 120° C. for 5 hr under Ar. Then, the reaction mixture was cooled to an ambient temperature and hexane (200 mL) was added. The mixture was stirred for 1 hr and the white precipitates were filtered, washed with hexane (~200 mL) and dried in vacuo to yield the ImesH$_2$-HCl salt (7.6 g, 96%). If necessary, the product can be further purified by washing with excess THF.

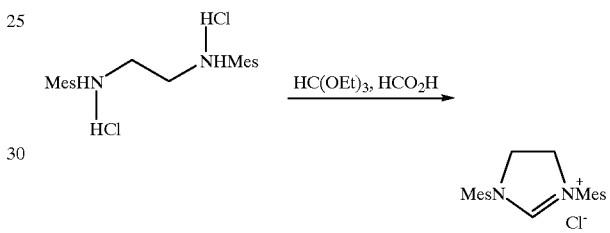

EXAMPLE 2

Selected NMR for 8: $^1$H NMR (C$_6$D$_6$): δ 6.76 (s, 2H), 5.99 (s, 1H), 2.78–2.67 (m, 3H), 2.44 (s, 9H), 2.14 (s, 9H), 2.14–2.09 (m, 8H), 1.69–1.58 (m, 14H), 1.28–1.17 (m, 8H), 1:12 (s, 9H). $^{31}$P NMR (C$_6$D$_6$): δ 17.4 (s).

RCM of substrates in Table 1 using catalyst generated in situ:

In a drybox, [(p-cymene)RuCl$_2$]$_2$ (0.02 mmol), ligand 1Cl (0.045 mmol), and NaO$^t$Bu (0.045 mmol) were weighed directly into a screw cap vial. A stir bar was added followed by 2 mL hexanes. Substrate (0.85 mmol) and tert-butyl acetylene (0.045 mmol) were added and the vial was sealed with a PTFE lined cap. The vial was removed from the drybox and stirred at 80° C. The reaction was monitored by GC and after complete consumption of substrate, the products were purified by chromatography on silica gel.

EXAMPLE 3

Using in-situ generated catalysts in a two-component system

Component (A)

A 50 gram mass of DCPD (containing 24 wt % trimerized DCPD) was added to a glass septum bottle containing 0.08 grams of [RuCl$_2$(p-cymene)]$_2$ and a Teflon-coated stirbar. The bottle was sealed with a rubber septum and purged with argon. The mixture was stirred at room temperature (22–25° C.).

Component (B)

A 50 gram mass of DCPD (containing 24 wt % trimerized DCPD) was added to a glass septum bottle containing 0.22 grams of sIMES-HCCl₃ and a Teflon-coated stirbar. The bottle was sealed with a rubber septum and purged with argon. Approximately 0.06 mL of phenylacetylene was transferred to the bottle via a syringe and the mixture was stirred at room temperature (22–25° C.).

After 24 hours at room temperature (22–25° C.), no apparent reaction had taken place in either Component (A) or Component (B). Component (A) was added to Component (B) and the mixture was heated in an oil bath at 90° C. Upon heating, the mixture formed a soft solid polymer.

EXAMPLE 4

A 100 gram mass of DCPD (containing 24 wt % trimerized DCPD) was added to a glass septum bottle containing 0.08 grams of [RuCl₂(p-cymene)]₂, 0.22 grams of sIMES-HCCl₃ and a Teflon-coated stirbar. The bottle was sealed with a rubber septum and purged with argon. Approximately 0.06 mL of phenylacetylene was transferred to the bottle via a syringe and the mixture was stirred at room temperature (22–25° C). After 24 hours at room temperature (22–25° C.) no apparent reaction had taken place. The mixture was heated in an oil bath at 90° C. Upon heating, the mixture formed a soft solid polymer.

EXAMPLE 5

A 75 gram mass of DCPD (containing 24 wt % trimerized DCPD) was added to a glass septum bottle containing 0.02 grams of [RuCl₂(p-cymene)]₂, 0.06 grams of sIMES-HCCl₃ and a Teflon-coated stirbar. The bottle was sealed with a rubber septum and purged with argon. Approximately 0.02 mL of tert-butylacetylene was transferred to the bottle via a syringe and the mixture was stirred at room temperature (22–25° C.). After 24 hours at room temperature (22–25° C.) no apparent reaction had taken place. The mixture was heated in an oil bath at 90° C. Upon heating, the mixture formed a soft rubberlike polymer.

EXAMPLE 6

A 75 gram mass of DCPD (containing 24 wt % trimerized DCPD) was added to a glass septum bottle containing 0.02 grams of [RuCl₂(p-cymene)]₂, 0.05 grams of 1,3-bis(2, 4, 6-trimethylphenyl)-4,5-dihydroimidazolium chloride, and 0.06 potassium tert-butoxide and a Teflon-coated stirbar. The bottle was sealed with a rubber septum and purged with argon. After 2 hours at room temperature (22–25° C.) the mixture formed a low molecular weight gel. The mixture was placed in a laboratory oven for 1 hour at 140° C. Upon heating, the mixture formed a soft rubberlike polymer.

EXAMPLE 7

A 75 gram mass of DCPD (containing 24 wt % trimerized DCPD) was added to a glass septum bottle containing 0.02 grams of [RuCl₂(p-cymene)]₂, 0.06 grams of sIMES-HCCl₃ and a Teflon-coated stirbar. The bottle was sealed with a rubber septum and purged with argon. After 8 hours at room temperature (22–25° C.) no apparent reaction had taken place. The mixture was heated in an oil bath at 90° C. Upon heating, the mixture formed a soft rubberlike polymer.

EXAMPLE 8

A 75 gram mass of DCPD (containing 24 wt % trimerized DCPD) was added to a glass septum bottle containing 0.06 grams of RuCl₂(p-cymene)PCy₃, 0.09 grams of sIMES-HCCl₃ and a Teflon-coated stirbar. The bottle was sealed with a rubber septum and purged with argon. The mixture was heated in an oil bath at 80° C. Upon heating, the mixture formed a hard solid polymer.

EXAMPLE 9

A 75 gram mass of DCPD (containing 24 wt % trimerized DCPD) was added to a glass septum bottle containing 0.06 grams of RuCl₂(p-cymene)PCy₃, 0.09 grams of sIMES-HCCl₃ and a Teflon-coated stirbar. The bottle was sealed with a rubber septum and purged with argon. Approximately 0.02 mL of phenylacetylene was transferred to the bottle via a syringe and the mixture was heated in an oil bath at 80° C. Upon heating, the mixture formed a soft solid polymer.

EXAMPLE 10

A 75 gram mass of DCPD (containing 24 wt % trimerized DCPD) was added to a glass septum bottle containing 0.02 grams of [RuCl₂(p-cymene)]₂, 0.05 grams of 1,3-bis(2, 4, 6-trimethylphenyl)-4,5-dihydroimidazolium chloride, and 0.06 potassium tert-butoxide and a Teflon-coated stirbar. The bottle was sealed with a rubber septum and purged with argon.

Approximately 0.02 mL of phenylacetylene was transferred to the bottle via a syringe and the mixture was heated in an oil bath at 80° C. Upon heating, the mixture formed a low molecular weight gel.

What is claimed is:

1. A process for the in-situ generation of a metathesis active catalyst of the formula:

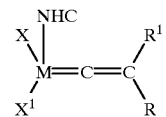

comprising:
   contacting an NHC carbene with a dimer of the formula [(arene)MX¹X]₂ and an alkyne of the formula RC≡CR¹; wherein
   M is ruthenium or osmium;
   X and X¹ are the same or different and are each independently an anionic ligand;
   NHC is any N-heterocyclic carbene ligand; and,
   R and R¹ are each independently hydrogen or a substituted or unsubstituted substituent selected from the group consisting of C₁–C₂₀ alkyl, C₂–C₂₀ alkenyl, C₂–C₂₀ alkynyl, aryl, C₁–C₂₀ carboxylate, C₁–C₂₀ alkoxy, C₂–C₂₀ alkenyloxy, C₂–C₂₀ alkynyloxy, aryloxy, C₂–C₂₀ alkoxycarbonyl, C₁–C₂₀ alkylthio, C₁–C₂₀ alkylsulfonyl and C₁–C₂₀ alkylsulfinyl.

2. The process of claim 1 wherein the arene is p-cymene.

3. The process of claim 1 wherein the R or R¹⁰ substituent group is substituted with one or more moieties selected from the group consisting of C₁–C₁₀ alkyl, C₁–C₁₀ alkoxy, and aryl, and wherein the moiety is substituted or unsubstituted.

4. The process of claim 3 wherein the moiety is substituted with one or more groups selected from the group consisting of halogen, a C₁–C₅ alkyl, C₁–C₅ alkoxy, and phenyl.

5. The process of claim 1 wherein at least one of X, X¹, NHC, R and R¹ are linked with at least one other of X, X¹, NHC, R, and R¹ to form a bidentate or multidentate ligand.

6. The process of claim 1 wherein at least one of X, X¹, NHC, R and R¹ includes one or more functional groups selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

7. The process of claim 1 wherein the NHC is selected from the group consisting of

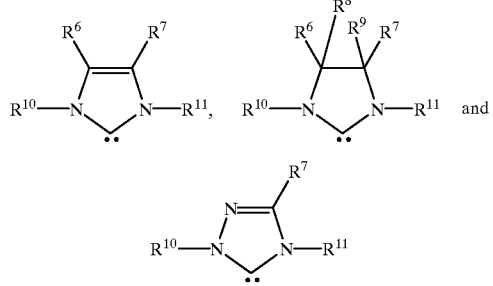

and

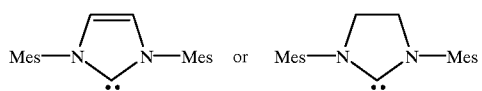

wherein $R^6$, $R^7$, $R^8$, $R^9$, $R^{10}$ and $R^{11}$ are each independently hydrogen or a substituted or unsubstituted substituent selected from the group consisting of $C_1-C_{20}$ alkyl, $C_2-C_{20}$ alkenyl, $C_2-C_{20}$ alkynyl, aryl, $C_1-C_{20}$ carboxylate, $C_1-C_{20}$ alkoxy, $C_2-C_{20}$ alkenyloxy, $C_2-C_{20}$ alkynyloxy, aryloxy, $C_2-C_{20}$ alkoxycarbonyl, $C_1-C_{20}$ alkylthio, $C_1-C_{20}$ alkylsulfonyl and $C_1-C_{20}$ alkylsulfinyl.

8. The process of claim 7 wherein at least one of $R^6$, $R^7$, $R^8$, $R^{9, R10}$ and $R^{11}$ is substituted with one or more moieties selected from the group consisting of $C_1-C_{10}$ alkyl, $C_1-C_{10}$ alkoxy, and aryl, wherein the moiety is substituted or unsubstituted.

9. The process of claim 8 wherein the moiety is substituted with one or more groups selected from the group consisting of halogen, a $C_1-C_5$ alkyl, $C_1-C_5$ alkoxy, and phenyl.

10. The process of claim 1 wherein:
M is Ru;
NHC is

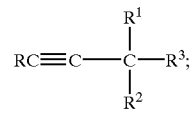

Mes is 2,4,6-trimethylphenyl;
X and $X^1$ are the same or different and are selected from the group consisting of halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate; and
R is hydrogen and the $R^1$ is selected from the group consisting of $C_1-C_{20}$ alkyl, $C_2-C_{20}$ alkenyl, and aryl.

11. The process of claim 1 wherein the arene is p-cymene and X and $X^1$ are each chloride.

12. The process of claim 1 wherein the alkyne is acetylene.

13. The process of claim 1 wherein the catalyst is generated in the absence of a solvent.

14. A process for the in-situ generation of a metathesis active catalyst of the formula:

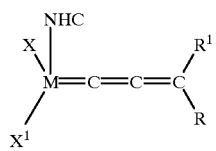

comprising:
contacting an NHC carbene with a dimer of the formula $[(arene)MX^1X]_2$ and an alkyne of the formula

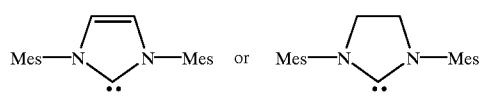

wherein
M is ruthenium or osmium;
X and $X^1$ are the same or different and are each independently an anionic ligand;
NHC is any N-heterocyclic carbene ligand;
R, $R^1$, and $R^2$ are each independently hydrogen or a substituted or unsubstituted substituent selected from the group consisting of $C_1-C_{20}$ alkyl, $C_2-C_{20}$ alkenyl, $C_2-C_{20}$ alkynyl, aryl, $C_1-C_{20}$ carboxylate, $C_1-C_{20}$ alkoxy, $C_2-C_{20}$ alkenyloxy, $C_2-C_{20}$ alkynyloxy, aryloxy, $C_2-C_{20}$ alkoxycarbonyl, $C_1-C_{20}$ alkylthio, $C_1-C_{20}$ alkylsulfonyl, and $C_1-C_{20}$ alkylsulfinyl; and
$R^3$ is OH.

15. The process of claim 14 wherein
M is Ru;
NHC is

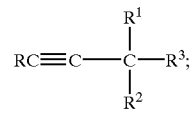

Mes is 2,4,6-trimethyiphenyl;
X and $X^1$ are the same or different and are selected from the group consisting of halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeG, EtO, tosylate, mesylate, and trifluoromethanesulfonate;
R is hydrogen; and
$R^1$ and $R^2$ are selected from the group consisting of $C_1-C_{20}$ alkyl, $C_2-C_{20}$ alkenyl, and aryl.

* * * * *